US009884037B2

(12) United States Patent
Li

(10) Patent No.: US 9,884,037 B2
(45) Date of Patent: *Feb. 6, 2018

(54) PHARMACEUTICAL COMPOSITION CONTAINING 8 TRIGLYCERIDES, AND PREPARATIONS AND USE THEREOF

(71) Applicant: ZHEJIANG KANGLAITE GROUP CO., LTD., Hangzhou, Zhejiang (CN)

(72) Inventor: Dapeng Li, Zhejiang (CN)

(73) Assignee: ZHEJIANG KANGLAITE GROUP CO., LTD., Xiasha Economic And Technological Development Zone, Hangzhou, Zhejiang (CN)

( * ) Notice: Subject to any disclaimer, the term of this patent is extended or adjusted under 35 U.S.C. 154(b) by 135 days.

This patent is subject to a terminal disclaimer.

(21) Appl. No.: 14/733,050

(22) Filed: Jun. 8, 2015

(65) Prior Publication Data

US 2016/0015671 A1 Jan. 21, 2016

(30) Foreign Application Priority Data

Jul. 18, 2014 (CN) .......................... 2014 1 0342495

(51) Int. Cl.
| | |
|---|---|
| *A61K 9/00* | (2006.01) |
| *A61K 9/48* | (2006.01) |
| *A61K 31/231* | (2006.01) |
| *A61K 45/06* | (2006.01) |
| *A61K 31/23* | (2006.01) |
| *A61K 35/00* | (2006.01) |

(52) U.S. Cl.
CPC .......... *A61K 31/231* (2013.01); *A61K 9/0019* (2013.01); *A61K 9/4833* (2013.01); *A61K 9/4858* (2013.01); *A61K 9/4866* (2013.01); *A61K 31/23* (2013.01); *A61K 35/00* (2013.01); *A61K 45/06* (2013.01)

(58) Field of Classification Search
CPC .. A61K 9/0019; A61K 9/4833; A61K 31/231; A61K 45/06; A61K 9/4858; A61K 31/23; A61K 35/00
USPC ......................................................... 424/451
See application file for complete search history.

(56) References Cited

U.S. PATENT DOCUMENTS

2014/0370129 A1* 12/2014 Li ...................... A61K 36/8994
424/750

OTHER PUBLICATIONS

Asian Pacific J Cancer Prey, 13 (10), 5319-5321.*

* cited by examiner

*Primary Examiner* — Snigdha Maewall
(74) *Attorney, Agent, or Firm* — Global IP Services; Tianhua Gu

(57) ABSTRACT

The present invention relates to a pharmaceutical composition containing 8 compounds: trilinolein, 1-olein-2,3-dilinolein, 1-palmitin-2,3-dilinolein, 1,3-diolein-2-linolein, 1-palmitin-2-linolein-3-olein, 1,3-dipalmitin-2-linolein, triolein and 1-palmitin-2,3-diolein. The invention also relates to pharmaceutical preparations of this composition and the use thereof in the treatment of tumors and in the immuno-enhancement.

18 Claims, No Drawings

PHARMACEUTICAL COMPOSITION CONTAINING 8 TRIGLYCERIDES, AND PREPARATIONS AND USE THEREOF

CROSS REFERENCE TO RELATED PATENT APPLICATION

The present application claims a priority of the Chinese patent application CN201410342495.6 with filing date Jul. 18, 2014, which application is incorporated herein by reference.

FIELD OF THE INVENTION

The present invention relates to the pharmaceutical field, specifically, the present invention relates to a pharmaceutical composition containing 8 triglycerides, the pharmaceutical preparations thereof, a process for the preparation of same and the use thereof in the treatment of tumors and in the immuno-enhancement.

BACKGROUND OF THE INVENTION

Coix seeds are dried ripe seeds of Coix lacryma-jobi L. var ma-yuen (Roman.), Stapf, a genus of plant in the Poaceae family. It is a dampness-eliminating drug and has been used as a medicinal and edible plant for a long time. Modern researches have found that Coix seeds have many pharmacological effects, such as analgesic, anti-inflammatory, immunomodulatory, anti-ulcer, hypolipidemic and anti-obesity effects. In recent years, researchers around the world have studied the chemical composition of the Coix seed by using TLC, HPLC-MS, GC, etc., and found a variety of active ingredients in it, including coixenolide, triglycerides, fatty acids, lactams, coix lactones, saccharides, sterols and triterpenoids. Among them, esters are the first discovered components having anti-tumor activities and the most reported chemical composition attracting the most attention. Kanglaite injection, in which the active ingredient is Coix seed oil, has been widely used in present Chinese clinical applications. However, there is rarely report on the substance basis and active antitumor ingredients. Xiang zhiming, at al, have analyzed qualitatively triglycerides in Coix seed oil and presumed tentatively 12 triglycerides: trilinolein, olein-dilinolein, palmitin-dilinolein, diolein-linolein, palmitin-linolein-olein, dipalmitin-linolein, triolein, olein-linolein-stearin, palmitin-diolein, palmitin-linolein-stearin, dipalmitin-olein and diolein-stearin (China Journal of Chinese Materia Medica, 2005, 30 (18): 1436-1438). However, they have not further studied the specific chemical structures and pharmacological activities of these ingredients. In fact, Coix seed oil also contains monoglycerides, diglycerides and fatty acid esters, etc. It can be seen that Coix seed contains complex components. This will inevitably be a great challenge for the quality control in the practical production process and the safety in clinical applications.

Therefore, the development of a safe, effective and controllable medicine for the treatment of tumors became a focused issue of the invention. In the present invention, triglyceride ingredients have been isolated from Coix seed oil one by one, their structures have been confirmed and their pharmaceutical activities have been screened. Among them, the inventors have selected 8 triglycerides having obvious antitumor and immuno-enhancement. These 8 triglycerides have been combined in different ratios and their pharmacodynamic tests have been conducted. Thus, the pharmaceutical composition of the invention and pharmaceutical preparations thereof have been obtained, and the uses thereof in the treatment of tumors and in the immuno-enhancement have been provided. The use of the pharmaceutical composition of the invention, having confirmed ingredients and definite composition, in medication can ensure the stability of quality in each batch in the industrial production and avoid toxic and side effects induced by the complication of ingredients in crude Coix seed oil when it is directly adopted.

SUMMARY OF THE INVENTION

The first aspect of the invention is to provide a pharmaceutical composition containing glycerides, specifically, 8 ingredients in the following mass percentages:

| | |
|---|---|
| trilinolein | 2.08-2.99 |
| 1-olein-2,3-dilinolein | 24.24-34.85 |
| 1-palmitin-2,3-dilinolein | 3.44-4.95 |
| 1,3-diolein-2-linolein | 22.32-32.09 |
| 1-palmitin-2-linolein-3-olein | 10.32-14.84 |
| 1,3-dipalmitin-2-linolein | 0.40-0.58 |
| triolein | 12.80-18.40 |
| 1-palmitin-2,3-diolein | 4.40-6.33 |

Preferably, the 8 ingredients are in the following mass percentages:

| | |
|---|---|
| trilinolein | 2.34-2.86 |
| 1-olein-2,3-dilinolein | 27.27-33.33 |
| 1-palmitin-2,3-dilinolein | 3.87-4.73 |
| 1,3-diolein-2-linolein | 25.11-30.69 |
| 1-palmitin-2-linolein-3-olein | 11.61-14.19 |
| 1,3-dipalmitin-2-linolein | 0.45-0.55 |
| triolein | 14.40-18.40 |
| 1-palmitin-2,3-diolein | 4.95-6.05 |

More preferably, the 8 ingredients are in the following mass percentages:

| | |
|---|---|
| trilinolein | 2.55-2.65 |
| 1-olein-2,3-dilinolein | 29.69-30.91 |
| 1-palmitin-2,3-dilinolein | 4.21-4.39 |
| 1,3-diolein-2-linolein | 27.34-28.46 |
| 1-palmitin-2-linolein-3-olein | 12.64-13.16 |
| 1,3-dipalmitin-2-linolein | 0.49-0.51 |
| triolein | 15.68-16.32 |
| 1-palmitin-2,3-diolein | 5.39-5.61 |

The above 8 triglyceride ingredients can be isolated by using the method described in the examples of the description, or prepared by using conventional synthesis in the art, or purchased from markets.

The second aspect of the invention is to provide a pharmaceutical preparation containing glycerides, specifically, it comprises a therapeutically effective amount of the pharmaceutical composition of the invention and one or more pharmaceutically acceptable carriers, wherein pharmaceutically acceptable carriers are selected from pharmaceutical conventional dilutions, excipients, fillers, emulsifiers, binders, lubricants, absorption accelerators, surfactants, disintegrants, lubricants and antioxidants, if necessary, flavoring agents, sweeteners, preservatives and/or coloring agents.

Pharmaceutically acceptable carriers can be selected from one or more in the group consists of: mannitol, sorbitol, sodium metabisulfite, sodium bisulfite, sodium thiosulfate, cysteine hydrochloride, thioglycolic acid, methionine, soybean lecithin, vitamin C, vitamin E, EDTA disodium, EDTA calcium sodium, monovalent alkali metal carbonate, acetate, phosphate or its aqueous solution, hydrochloric acid, acetic acid, sulfuric acid, phosphoric acid, amino acids, sodium chloride, potassium chloride, sodium lactate, ethylparaben solution, benzoic acid, potassium sorbate, chlorhexidine acetate, xylitol, maltose, glucose, fructose, dextran, glycine, starch, sucrose, lactose, mannitol, silicic derivatives, cellulose and its derivatives, alginates, gelatin, polyvinyl pyrrolidone, glycerin, Tween 80, agar-agar, calcium carbonate, calcium bicarbonate, surfactants, polyethylene glycol, cyclodextrin, 3-cyclodextrin, phospholipid material, kaolin, talc, and calcium stearate or magnesium stearate.

The pharmaceutical preparation can be an oral solid preparation, an oral liquid preparation or an injection.

Preferably, the oral solid preparation is selected from any one of capsules, tablets, dripping pills, granules, and concentrated pills; the oral liquid preparation is selected from any one of aqueous or oily suspensions, solutions, emulsions, syrups or elixirs, and a dry product that may be reconstructed by water or other suitable carrier before use; and the injection is selected from any one of nano suspensions, liposomes, emulsions, lyophilized powder for injection and aqueous injections.

More preferably, the injection comprises the following components: the pharmaceutical composition of the invention 50-350 g, soybean lecithin for injection or soybean lecithin acceptable for injection 10-40 g, glycerin for injection or glycerin acceptable for injection 15-50 g, and water for injection adds to 1000 mL.

The injection of the invention can be prepared by a method comprising steps of:

adding appropriate amount of water for injection to A formulated amount of soybean lecithin for injection or soybean lecithin acceptable for injection; dispersing the mixture with a high shear dispersing emulsifier to give a dispersion without bulks or granules; adding A formulated amount of glycerin for injection or glycerin acceptable for injection; then adding water for injection to a specified amount, and stirring the mixture to give a water phase;

weighing A formulated amount of the pharmaceutical composition of the invention; heating the weighed oil and the water phase separately to 60-70° C., then mixing them and emulsifying the mixture in a high pressure homogenizer, in which the low pressure is 5-12 MPa and the high pressure is 25-50 MPa; repeating the cycle of homogenization for 3-6 times until the amount of particles below 2 μm is no less than 95% and particles above 5 μm are undetectable; if necessary, using NaOH or HCl to adjust the pH to 4.8 to 8.5, preferably 6.8 to 7.0, most preferably 6.8; and filtering the resulting homogeneous emulsion by nitrogen pressure through a microporous filter of 3 μm or less; filling the emulsion with nitrogen, sterilizing and cooling to afford the injection.

The capsule of the invention comprises the following components: the pharmaceutical composition of the invention 200-800 g, antioxidant(s) and/or emulsifier(s) 0.20-0.60 g for 1000 capsules.

The capsule of the invention can be prepared by a method comprising steps of:

preparing glue solution: weighing gelatin, purified water, glycerin and a preservative at a weight ratio of 1:0.6-1.2:0.3-0.8:0.0001-0.01; adding glycerin, purified water and preservative (selected from any one of 10% ethylparaben solution, benoic acid, potassium sorbate and chlorhexidine acetate) sequentially into a glue melting tank; heating to 70° C.-90° C.; then adding gelatin and constantly stirring the mixture under vacuum until the gelatin is completely dissolved; filtering the glue solution and storing the filtered glue solution at 56-62° C. for use;

preparing drug liquid: adding formulated amount of Coix seed oil, antioxidant (Vitamin E) and/or emulsifier (Tween 80) into an dosing tank, and stirring the mixture constantly until being homogeneously mixed; and pressing capsules: choosing proper pellet dies according to the capsule size; pressing capsules in a temperature of 15-30° C. and a relative humidity of less than 35%; drying the pressed and shaped capsules; after removing capsules of abnormal size, washing the normal capsules with 95% medicinal ethanol, and drying them continuously to a moisture content of less than 12%; visually inspecting and removing unqualified capsules; finally printing and packaging to afford the capsules.

It is demonstrated, in pharmacodynamic experiments, that the pharmaceutical composition of the invention and pharmaceutical preparations thereof have shown different degrees of inhibition on a variety of human tumor cell lines. Thus, they can be used to treat neoplastic diseases.

Therefore, another aspect of the invention is to provide a method of the treatment of a tumor or the enhancement of immunity in a mammal (including human), comprising administering to the mammal (including human) in need a therapeutically effective amount of the pharmaceutical composition of the invention or a pharmaceutical preparation thereof.

The pharmaceutical composition of the invention or the pharmaceutical preparation thereof can be administered alone or in combination with LAK cells (lymphokines activated killer cells).

Preferably, the tumor refers to lung cancer, liver cancer, pancreatic cancer, prostate cancer, ovarian cancer or breast cancer, in early, middle or late stage.

The following experimental data are used to illustrate benefical effects of the pharmaceutical composition of the invention and the pharmaceutical preparations thereof in anti-tumor and immuno-enhancement.

I. Inhibition of the Pharmaceutical Composition of the Invention and Preparations Thereof on 8 Human Tumor Cell Lines in MTT Method In Vitro Experimental Materials and the Preparation Thereof:
(1) Cell lines: PANC-1 (human pancreatic cancer cells), SKOV3 (human ovarian cancer cells), MCF-7 (human breast cancer cells), Bcap-37 (human breast cancer cells), SMMC-7721 (human hepatic cancer cells), HepG-2 (human hepatic cancer cells), A549 (human lung cancer cells) and H460 (human lung cancer cells), storaged and passaged maintainably in Research and Evaluation Center for Pharmacology, Shanghai Institute of Pharmaceutical Industry;
(2) DMEM complete medium supplied with 10% newborn calf serum (GIBCO BRL), 1% of penicillin (100 U/mL)+streptomycin (100 μg/mL);
(3) 0.25% trypsin solution, purchased from Invitrogen Corp. and storaged at −20° C.;
(4) Phosphate buffer (PBS): NaCl 8 g, KCl 0.2 g, $Na_2HPO_4$ 1.15 g and $KH_2PO_4$ 0.2 g, dissolved in 1 L double-distilled water and autoclaved at 121° C. for 20 min, then storaged at 4° C.;
(5) MTT (AMRESCO) solution: 5 mg/ml in PBS;
(6) Formazan crystal dissolving solution: SDS 10 g, isobutanol 5 ml and concentrated hydrochloric acid 0.1 ml, dissolved in 100 ml of deionized double distilled water.

Experimental Method

The inhibition effects of samples on the above-mentioned cell lines were detected by using MTT method. The specific procedures were as follows:

(1) Cell culture: (a) Storaged cells were taken out from the liquid nitrogen, thawed quickly in a 37° C. water bath, then aseptically transferred into 6 ml of cellular medium in a 10 ml centrifugal tube, and centrifuged at 1000 rpm for 5 min. The supernatant was discarded, then the precipitated cells were re-suspensed in 5-6 ml cellular media by pipetting and transferred into a flask in a 37° C. incubator for cell culture; (b) Next day, the flask was taken out from the incubator and the used medium was discarded, then the cells were incubated in 5-6 ml fresh medium in the 37° C. incubator; (c) On the third day, the flask was taken out from the incubator and the used medium was discarded, then 2-3 ml of PBS (pH7.4) was added into the flask with rocking for cleaning it and the used PBS was discarded. Such a cellular cleaning step was repeated once again. 3-5 drops of 0.25% trypsin solution were added into the flask with sloshing, thus well-distributed in it. The flask was capped and placed in a 37° C. incubator for about 3 min, and the separation of cells from the flask wall was observed under the microscope. 2 ml of cellular medium was added and cells were separated completely from the flask wall by pipetting, then the cell suspension was transferred into 2 separate clean flasks, each containing 5-6 ml medium. The cell suspension was well-distributed by pipetting, then the flask was placed in a 37° C. incubator. (d) Step(c) was repeated every other day. In the whole cultivation process, adherent cells were not allowed to grow too dense and suspension cells were always maintained at a logarithmic growth stage.

(2) Preparation of the sample and the control: A proper amount of the pharmaceutical composition of the invention was dissolved in DMSO to obtain a solution in a concentration of 10 mg/ml. This solution was diluted in a gradient dilution with PBS to obtain a set of sample solutions in the concentration of 10 mg/ml, 5000 µg/ml, 2500 µg/ml, 1250 µg/ml, 625 µg/ml and 312.5 µg/ml, respectively.

(3) Each diluted sample solution was added into duplicated wells of a 96 well flat-bottom microplate (10 µl/well). The correspondingly diluted DMSO solutions, as controls, were added into the wells of the microplate.

(4) Cells in a logarithmic growth stage were trypsinized and washed, then re-suspended in the medium containing 10% calf serum. The number of living cells was counted in Trypan blue dye exclusion method and cell suspensions were adjusted into a density of $2 \times 10^5$ cell/ml.

(5) The cell-contained 96 well flat-bottom microplate was placed in a 37° C. incubator and cells were incubated under 5% $CO_2$ for 48 h.

(6) 20 µl of 5 mg/ml MTT solution was added into each well and cells were incubated continuously in the incubator for 3-4 h.

(7) 100 µl of crystal dissolving solution was added into each well and cells were incubated continuously in the incubator overnight, so as to dissolve the resulted formazan crystals sufficiently. Then, the absorbance value was measured at 570 nm for each well.

(8) Based on absorbance values, inhibition rates on the cell growth were calculated for sample groups of various concentrations. The calculation formula was as follows:

(1−mean absorbance of experimental wells/mean absorbance of control wells)×100%

Experimental Results

TABLE 1

Inhibition rates of samples in various concentrations on the growth of 8 cell lines (%)

| Cell line | Concentration of Sample | | | | | |
|---|---|---|---|---|---|---|
| | 1000 ug/ml | 500 µg/ml | 250 µg/ml | 125 µg/ml | 62.5 µg/ml | 31.25 µg/ml |
| PANC-1 | 98.65 | 77.03 | 27.97 | 20.98 | 16.87 | 2.77 |
| SKOV3 | 98.78 | 62.79 | 27.54 | 15.32 | 9.44 | 0.49 |
| MCF-7 | 98.33 | 61.56 | 26.19 | 10.94 | 7.87 | 0.36 |
| Bcap-37 | 99.23 | 73.07 | 36.30 | 15.02 | 2.70 | 1.52 |
| SMMC-7721 | 98.16 | 68.76 | 39.44 | 17.57 | 13.10 | 2.70 |
| HepG-2 | 97.91 | 67.30 | 33.40 | 27.05 | 19.16 | 2.08 |
| A549 | 99.05 | 75.98 | 56.16 | 42.33 | 20.08 | 0.47 |
| H460 | 97.38 | 74.78 | 55.75 | 43.24 | 16.29 | 7.56 |

TABLE 2

$IC_{50}$ values of samples in 8 cell lines in vitro (µg/ml)

| | Sample | |
|---|---|---|
| Cell line | Pharmaceutical composition of the invention | Positive control (Taxol) |
| PANC-1 | 207.8 | 0.44 |
| SKOV3 | 256.6 | 0.22 |
| MCF-7 | 280.6 | 0.18 |
| Bcap-37 | 234.4 | 0.28 |
| SMMC-7721 | 222.8 | 0.41 |
| HepG-2 | 219.1 | 0.45 |
| A549 | 189.0 | 0.46 |
| H460 | 167.1 | 0.49 |

Conclusion

The pharmaceutical composition of the invention and preparations thereof in various concentrations have shown inhibition effects on 8 human tumor cell lines in different degrees.

II. Effects of the Injection of the Invention on Immunological Functions in Mice Animals and Materials Animal:

Kunming, male, 18-22 g, provided by Shanghai Institute of Pharmaceutical Industry, Certificate of quality No. 107;

C57BL/6 mice, male, 18-20 g, provided by Shanghai Experimental Animal Center;

DBA/6 mice, male, 18-20 g, provided by Shanghai Experimental Animal Center, Certificate No. 005.

Materials:

Injection of the invention: prepared according to the invention by Zhijiang Hospital of Traditional Chinese Medicine;

Solvents (blank control): provided by Zhijiang Hospital of Traditional Chinese Medicine;

Lentinan (positive control): 4 mg/2 ml, produced by Fuzhou Meifeng Pharmaceutical Factory, Batch No. 911026;

Medium: RPMI1640 (Difco), containing 15% calf serum, mercaptoethanol and Hepes, etc.;

$^3$H-TdR (1 mci/ml): provided by Shanghai Institute of Atomic Nucleus;

Concanavalin (ConA): 50 µg/ml, Sigma;

YAC-1 cell strain, L1210 cell strain and CTLL cell strain: reserved in the applicant's laboratory.

Method and Results

1. Influence of the Injection of the Invention on the Splenic Lymphopoiesis Induced by ConA in Mice In Vitro Spleens were picked up from C57BL/6 mice in aseptic condition. Splenocytes were separated and the concentration of cells was adjusted to $1\times10^7$ cells/ml with RPMI 1640+ 15% FCS medium. The experiment groups were as follows: the injection of the invention in four concentrations, lentinan (positive control group) in four concentrations, corresponding solvent (blank control I) and medium (blank control II). 100 μl Cells, 100 μl solution of drug/control and 50 μl ConA were added in each well in triplicate. The 96 well microplate was incubated in a 37° C. incubator under 5% $CO_2$ for 48 h. $^3$H-TdR (0.5 μci/well) was added and the incubation was continued for 20 h. Cells were collected, and CPM values were determined in a liquid scintillation counter and compared with control groups. It is shown in the results (table 3) that the injection of the invention, as same as lentinan, obviously facilitated the splenic lymphopoiesis in mice in vitro and the effect is linear dependent to the concentration.

TABLE 3

Influence of the injection of the invention on the splenic lymphopoiesis in mice in vitro

| Group | Concentration (μl) | | CPM ($\bar{x}$ ± SD) |
|---|---|---|---|
| Injection of the invention | 100 | (1:4) | 7823 ± 1115** |
| Injection of the invention | 100 | (1:2) | 7216 ± 1054** |
| Injection of the invention | 100 | (1:1) | 6434 ± 958** |
| Injection of the invention | 100 | (stock solution) | 6107 ± 1097** |
| Lentinan | 100 | (1:4) | 11555 ± 1279** |
| Lentinan | 100 | (1:2) | 11025 ± 1133** |
| Lentinan | 100 | (1:1) | 7700 ± 747** |
| Lentinan | 100 | (stock solution) | 7420 ± 957** |
| Corresponding solvent | 100 | | 4612 ± 719 |
| Medium | 100 | | 4795 ± 487 |

**P < 0.01, Compared with control groups, corresponding solvent and medium

2. Influence of the Injection of the Invention on the Splenic Lymphopoiesis in Mice Bearing Cancer Each of 60 DBA/2 mice was inoculated subcutaneously with $1\times10^4$ L1210 leukemia cells of mice. Next day, the mice were grouped randomly into 6 groups (10 mice per group): Lentinan 20 mg/kg, the injection of the invention (6.25 ml/kg, 12.5 ml/kg and 25 ml/kg), solvent control and NS control. Animals were administered, i.v., for 7 days, then sacrificed. Spleens were picked up in aseptic condition. Spleens were homogenized and splenocytes were counted and adjusted into $1\times10^7$/ml. Cells (100 μl/well) and medium (100 μl/well) were added into wells of a 96 well microplate in triplicate. The 96 well microplate was incubated in a 37° C. incubator under 5% $CO_2$ for 48 h. Then, $^3$H-TdR (0.5 μci/well) was added and the incubation was continued for 20 h. Cells were collected, and CPM values were determined and compared with control groups. It is shown in the results (table 4) that the injection of the invention has obviously enhanced the splenic lymphopoiesis in mice bearing L1210 leukemia cells, and the immuno-enhancement effect has increased with the increasing dose. Lentinan has also shown immuno-enhancement effect.

TABLE 4

Influence of the injection of the invention on the splenic lymphopoiesis in mice bearing L1210 leukemia cells

| | Dose (ml/kg) | Dose regimen | No. | CPM ($\bar{x}$ ± SD) |
|---|---|---|---|---|
| Injection of the invention | 6.25 | iv × 7 | 10 | 8898 ± 436** |
| Injection of the invention | 12.5 | iv × 7 | 10 | 10776 ± 572** |
| Injection of the invention | 25.0 | iv × 7 | 10 | 14679 ± 587** |
| Lentinan | 20 mg/kg | iv × 7 | 10 | 7410 ± 770** |
| Solvent | 10.0 | iv × 7 | 10 | 5690 ± 1180$^\Delta$ |
| NS | 10.0 | iv × 7 | 10 | 5230 ± 455 |

**P < 0.01, compared with solvent or NS;
$^\Delta$P > 0.1, compared with NS.

3. Influence of the Injection of the Invention on the Activity of Natural Killer Cells (NK Cells) in Mice In Vitro Method: The activity of NK cells were detected by the inhibition on $^3$H-TdR incorporation.

Spleens were picked up from C57BL/6 mice in aseptic condition. Splenocytes, as effector cells, were adjusted to $1\times10^6$ cells/ml. YAC-1 cells, target cells, which have been cultured for 24 h, were adjusted to $1\times10^4$ cells/ml. The cells were added into wells of a 96 well microplate (100 μl/well). The experiment groups were as follows: the injection of the invention in four concentrations, lentinan (positive control group) in four concentrations, corresponding solvent (blank control I) and medium (blank control II). To each well of a 96 well microplate were added cells (Splenocytes: YAC-1=100:1) (100 μl), test sample (100 μl) and $^3$H-TdR 0.5 μci/well. After being incubated in a 37° C. incubator under 5% $CO_2$ for 24 h, cells were collected, and CPM values were determined. The specific percentage inhibition (Pi), indicating the activity of NK cells, was calculated according to the formula:

$$Pi=(1-CPM_{Exp.}/CPM_{cont.})\times100\%$$

It is shown in table 5 that the injection of the invention has, as same as lentinan, activated NK cells inordinately in mice in vitro, thus it possesses immune activation.

TABLE 5

Influence of the injection of the invention on the activity of NK cells in mice in vitro

| Group | Concentration (μl) | | CPM ($\bar{x}$ ± SD) | Pi % |
|---|---|---|---|---|
| Injection of the invention | 100 | (1:4) | 5902 ± 1104** | 51.76 |
| Injection of the invention | 100 | (1:2) | 6806 ± 1097** | 44.37 |
| Injection of the invention | 100 | (1:1) | 8402 ± 1287** | 31.33 |
| Injection of the invention | 100 | (stock solution) | 11023 ± 709 | 9.91 |
| Lentinan | 100 | (1:4) | 5544 ± 85** | 54.5 |
| Lentinan | 100 | (1:2) | 7892 ± 995** | 35.5 |
| Lentinan | 100 | (1:1) | 8130 ± 930** | 33.5 |
| Lentinan | 100 | (stock solution) | 8625 ± 1135 | 29.5 |
| Solvent (Controller I) | 100 | | 12710 ± 1125 | |
| Medium (Controller II) | 100 | | 12235 ± 725 | |

**P < 0.01, compared with solvent and medium control groups.

4. Influence of the Injection of the Invention on the Activity of NK Cells in Mice Bearing Cancer Each of 60 DBA/2 mice was inoculated subcutaneously with $1\times10^4$ L1210 leukemia cells of mice. Next day, the mice were grouped randomly into 6 groups (10 mice per group): Lentinan 20 mg/kg (positive control), the injection of the invention (6.25 ml/kg, 12.5 ml/kg and 25 ml/kg), solvent control and NS control. Animals were administered, i.v., for 7 days, then sacrificed. Spleens were picked up in aseptic condition. Splenocytes were prepared and adjusted into $1\times10^6$/ml. The activity of NK cells was detected by using the inhibition on $^3$H-TdR incorporation. To wells of a 96 well microplate were added splenocytes cells (effector cells) 100 μl/well, YAC-1 cells (target cells, $1\times10^4$ cells/ml) 100 μl/well and $^3$H-TdR 0.5 μci/well, in triplicate. After being incubated in a 37° C. incubator under 5% $CO_2$ for 24 h, cells were collected, and CPM values were determined. The specific percentage inhibition (Pi), indicating the activity of NK cells, was calculated according to the above formula.

It is shown in table 6 that the injection of the invention has, as same as lentinan, activated NK cells in mice bearing cancer, thus it possesses immune activation.

TABLE 6

Influence of the injection of the invention on the activity of NK cells in mice bearing cancer

| Group | Dose (ml/kg) | Dose regimen | No. | CPM ($\bar{x}$ ± SD) | Pi (%) |
|---|---|---|---|---|---|
| Injection of the invention | 6.25 | iv × 7 | 10 | 10409 ± 1598 | 16.39 |
| Injection of the invention | 12.5 | iv × 7 | 10 | 8126 ± 956** | 34.73 |
| Injection of the invention | 25.0 | iv × 7 | 10 | 6265 ± 901** | 49.68 |
| Lentinan | 20 mg/kg | iv × 7 | 10 | 5660 ± 260** | 54.5 |
| Solvent | 10.0 | iv × 7 | 10 | 12510 ± 430$^\Delta$ | |
| NS | 10.0 | iv × 7 | 10 | 12450 ± 340 | |

**P < 0.01, compared with solvent and NS control;
$^\Delta$P > 0.1, compared with NS.

5. Influence of the Injection of the Invention on the Production of IL-2 in Mice Bearing Cancer Each of 60 DBA/2 mice was inoculated subcutaneously with $1\times10^4$ L1210 leukemia cells of mice. Next day, the mice were grouped randomly into 6 groups (10 mice per group): Lentinan 20 mg/kg, the injection of the invention (6.25 ml/kg, 12.5 ml/kg and 25 ml/kg), solvent control and NS control. Animals were administered, i.v., for 7 days, then sacrificed. Spleens were picked up in aseptic condition. Splenocytes were prepared and adjusted into $1\times10^7$/ml. To each well of a 24 well plate were added splenocytes cells (2 ml) and Con A (5 μg/ml). After the plate was incubated in a 37° C. incubator under 5% $CO_2$ for 24 h, the supernate was collected. The activity of IL-2 was determined in IL-2 dependent CTLL cell strain by using the method of $^3$H-TdR incorporation.

As shown in table 7, the injection of the invention has promoted the production of IL-2 in animals bearing cancer and this effect increased in a dose-dependent way.

TABLE 7

Influence of the injection of the invention on the production of IL-2 in mice suffering from L1210 leukemia

| Group | Dose (ml/kg) | Dose regimen | No. | CPM ($\bar{x}$ ± SD) |
|---|---|---|---|---|
| Injection of the invention | 6.25 | iv × 7 | 10 | 1521 ± 192 |

TABLE 7-continued

Influence of the injection of the invention on the production of IL-2 in mice suffering from L1210 leukemia

| Group | Dose (ml/kg) | Dose regimen | No. | CPM ($\bar{x}$ ± SD) |
|---|---|---|---|---|
| Injection of the invention | 12.5 | iv × 7 | 10 | 2092 ± 390 |
| Injection of the invention | 25.0 | iv × 7 | 10 | 6102 ± 882** |
| Lentinan | 20 mg/kg | iv × 7 | 10 | 2750 ± 123** |
| Solvent | 10.0 | iv × 7 | 10 | 1750 ± 487$^\Delta$ |
| NS | 10.0 | iv × 7 | 10 | 1830 ± 95 |

**P < 0.01, compared with NS;
$^\Delta$P > 0.1, compared with NS.

6. Influence of the Injection of the Invention on the Phagocytosis of Macrophages of Mice Healthy Kunming mice, 18-22 g, were divided randomly into a treating group and a control group (corresponding solvent), i.p.×7 day. Each mouse was injected with 2% chicken erythrocytes (1 ml), i.p. after the final administration. 30 Min later, the mouse was sacrificed via cervical dislocation and fastened in a supine position. The skin in the middle of abdomen was scissored and 2 ml NS was injected into the abdominal cavity. The board was rotated for 1 min. 1 ml washing liquid was aspirated from the abdomen and dripped onto two glass slides. The glass slides were put into an enamel box padded with a wet gauze. After being incubated in a 37° C. incubator for 30 min, the glass slides were rinsed in NS to remove non-adherent cells and dried in the air. The slides were fixed with acetone-methanol (1:1) and dyed with 4% (v/v) Giemsa-phosphate buffer, then rinsed with distilled water thoroughly and dried.

100 macrophages were counted for one slide under oil immersion lens. Percentage of phagocytosis and index of phagocytosis were calculated according to the formulas:

Percentage of phagocytosis=(Count of cells having swallen chicken erythtocyte/100 macrophages)× 100%

Index of phagocytosis=Count of swallen chicken erythtocytes/100 macrophages

As shown in table 8, the injection of the invention (12.5 ml/kg, 6.25 ml/kg, i.p., ×7 days) has obviously promoted the phagocytic activity of peritoneal macrophages in mice.

TABLE 8

Activation of the injection of the invention on peritoneal macrophages in mice

| | | | | Phagocytosis on chicken erythtocyte | |
|---|---|---|---|---|---|
| | Dose (ml/kg) | Dose regimen | No. | Percentage of phago-cytosis (%) $\bar{x}$ ± SD | Index of phago-cytosis $\bar{x}$ ± SD |
| Injection of the invention | 6.25 | ip × 7 | 10 | 32.01 ± 1.89 | 0.72 ± 0.07** |
| Injection of the invention | 12.5 | ip × 7 | 10 | 52.78 ± 3.43 | 1.79 ± 0.11** |
| Solvent | 12.5 | ip × 7 | 10 | 14.00 ± 1.08 | 0.34 ± 0.03 |

**P < 0.01, compared with control.

Conclusion:

The injection of the invention has shown an acceleration on splenic lymphopoiesis in mice, an activation on the activity of NK cells in mice bearing cancer, an enhancement on the production of IL-2 in mice bearing cancer, and an obvious promotion on the phagocytic activity of peritoneal macrophages in mice. Thus, the injection of the invention can enhance immunity and this is in favour of anti-tumor effects.

III. Influence of the Injection of the Invention on the Curative Effect of LAK Cells Materials & Methods Sample: The injection of the invention, provided by Pharmaceutical Lab., Zhijiang Hospital of Traditional Chinese Medicine, Batch 930924, stored in 4° C. refrigerator;

Target cells: K562 cells, Daudi cell, introduced from Japanese National Cancer Research Center;

Activating fluid: RPMI 1640 medium+10% inactivated human AB-type serum+2 mM glutamine+100 U/ml penicilin+100 µg/ml streptomycin+rIL-2, used for the introduction of LAK cells;

Nutrient solution: RPMI 1640 medium+10% neonatal bovine serum (NBS)+2 mM glutamine+100 U/ml penicilin+100 gig/ml streptomycin, used for the culture of target cells.

Introduction of LAK Cells:

To the peripheral blood of healthy donators was added lymphocyte separating medium. Mononuclear cells obtained by centrifuging this suspension were washed with Hanks solution twice and suspended, in a concentration of $1\times10^6$/ml, in LAK cells activating fluid containing RPMI 1640 medium, penicilin, streptomycin, glutamine, inactivated human AB-type serum and rIL-2. The cells were cultured for 10 days, centrifuged for 15 min, washed with Hanks solution twice and suspended in NS injection containing 5% serum albumin of average persons and rIL-2. NK activity was indicated as killing activity of mononuclear cells separated from the peripheral blood of healthy donators.

Treatment of Tumor Cells with the Injection of the Invention:

Tumor cells used were K562 cells sensitive to NK cells and Daudi cells tolerant to NK cells. To the suspension of tumor cells ($1\times10^5$/ml) was added the injection of the invention (diluted with RPMI 1640 medium in 1:8) in a ratio of 1:1. After being treated for 2 h, the cell suspension served as target cells.

Test of Cell Killing Activity:

Effector cells were washed with RPMI 1640 medium for 3 times and suspended. The suspended effector cells and/or target cells were added into each well of 96 well U bottom microplate (effector cells:target cells=15:1). After adding 0.5 µci $^3$H-TdR (10 µl/well), the microplate was incubated for 18 h. Then the reaction was terminated and CPM values were determined. The killing activity was calculated according to the formula of:

Killing activity (%)=$((B+C-A)/C)\times100$

A: CPM of the well having effector cells and target cells;
B: CPM of the well having effector cells alone;
C: CPM of the well having target cells alone.

Results:

1. NK Activity: Killing activity of NK cells on K562 cells treated with the injection of the invention for 2 h had no change, but on Daudi cells, increased from 4.8% to 11.2% ($P<0.01$).

2. LAK Activity: Similarly, LAK Activity on K562 cells treated with the injection of the invention had no change, but on Daudi cells, increased from 30.9% to 44.6% ($P<0.01$).

Discussion:

Killing activities of LAK cells and NK cells on Daudi cells treated with the injection of the invention have significantly enhanced. The injection of the invention can enhance body immunity and shows synergistic effects in combination with LAK therapy.

It is proved by experiments that all pharmaceutical compositions containing glycerides and pharmaceutical preparations thereof in various contents described in the Specification can obtain effects shown in the above experiment examples.

The following examples further illustrate the invention, but are not construed as a limitation to the invention.

DETAILED DESCRIPTION OF THE PREFERRED EMBODIMENTS

Example 1 Preparation of *Coix* Seed Oil 1000 g of *Coix* seeds having moisture content ≤10% were crushed into 100 mesh powder and extracted by using a supercritical $CO_2$ extraction system, in which the extraction temperature was 50° C., the extraction pressure was 22 Mpa, the separation temperature was 40° C., the separation pressure was 8 Mpa, and the flow rate of liquid $CO_2$ was 500 L/h. A continuous extraction for 3 h afforded a crude *Coix* seed oil. To the crude *Coix* seed oil was added 46% petroleum ether by weight of the crude oil and 1% NaOH aqueous solution to alkali-refine the crude *Coix* seed oil. After layering, the upper organic phase was added with 5% activated neutral alumina by weight of the crude oil, and filtered. The filtrate was heated to 40-50° C. and added with 4% activated kaolin by weight of crude oil, then filtered. The filtrate was concentrated under a reduced pressure to remove the solvent, and added with activated neutral alumina (10% of the oil weight). The mixture was filtered, and the filtrated oil was sterilized by dry heating under vacuum at 150-180° C. After cooling, the oil was filtered to obtain *Coix* seed oil.

Example 2 Preparation of Trilinolein

Isolation was carried out on P3000A preparative high performance liquid chromatography (Column: Superstar Benetnach™ $C_{18}$ 20 mm×150 mm, 5 µm; Mobile phase A: acetonitrile, Mobile phase B: acetonitrile-tetrahydrofuran (1:1)). *Coix* seed oil solution was prepared with mobile phase B into 50 mg/mL. Injection volume of each separation was 1.5 mL. Gradient conditions were: mobile phase B: 0-27 min: 50%-60%, 27-35 min: 90%, 35-45 min: 100%; and flow rate: 18 mL/min. UV detection wavelength: 208 nm. Peak fractions at retention time of 12.6-14.2 min were collected, and concentrated using a rotary evaporator in vacuum under nitrogen. Residues were transferred with chloroform to a 10 mL vial, and dried in a vacuum oven at 35° C. for 6 h. After filling with nitrogen, the dried samples were frozen in a refrigerator to give the trilinolein.

HR-EI-MS: m/z=878.7344 (Calcd.=878.7363, $C_{57}H_{98}O_6$), Degree of unsaturation=9.

IR (KBr film): 1746, 1170, 1098; 2928, 2856, 724; 3008, 1655 $cm^{-1}$ (weak).

1H-NMR data are shown in Table 9.

13C-NMR data are shown In Table 10.

TABLE 9

¹H-NMR spectral data of the compounds of Examples 2-9

| No. | G-H | H | 2-H | 3-H | 4-H | 5-H | 6-H | 7-H | 8-H | 9-H | 10-H | 11-H | 12-H | 13-H | 14-H | 15-H | 16-H | 17-H | 18-H |
|---|---|---|---|---|---|---|---|---|---|---|---|---|---|---|---|---|---|---|---|
| A | α | 4.30 | | | | | | | | | | | | | | | | | |
| LLL | β | 5.27 | 2.32 | 1.61 | | 1.32 | | | 2.05 | 5.36 | | 2.77 | 5.36 | | 2.05 | | 1.32 | | 0.89 |
| | α' | 4.15 | | | | | | | | | | | | | | | | | |
| B | α | 4.29 | | | | | | | | | | 2.77 | 5.37 | | 2.04 | | | | |
| OLL | β | 5.27 | 2.32 | 1.61 | | 1.33 | | | 2.04 | 5.37 | | | | | | | 1.33 | | 0.88 |
| | α' | 4.14 | | | | | | | | | | 2.04 | | 1.33 | | | | | |
| C | α | 4.30 | | | | | | | 2.05 | 5.36 | | 2.77 | 5.36 | | 2.05 | | 1.31 | | 0.88 |
| PLL | β | 5.27 | 2.31 | 1.61 | | 1.31 | | | | | | | | | | | | | |
| | α' | 4.15 | | | | | | | 1.31 | | | | | 1.31 | | | 0.88 | | |
| D | α | 4.30 | | | | | | | | | | 2.05 | | 1.32 | | | 1.32 | | 0.89 |
| OLO | β | 5.27 | 2.32 | 1.61 | | 1.32 | | | 2.05 | 5.36 | | | | | | | | | |
| | α' | 4.15 | | | | | | | | | | 2.77 | 5.36 | | 2.05 | | | | |
| E | α | 4.15 | | | | | | | 2.04 | 5.35 | | 2.04 | | 1.28 | | | 1.28 | | 0.88 |
| PLO | β | 5.27 | 2.31 | 1.61 | | 1.28 | | | | | | 2.77 | 5.35 | | 2.04 | 1.28 | | | |
| | α' | 4.30 | | | | | | | 1.28 | | | | | | | | 0.88 | | |
| F | α | 4.15 | | | | | | | 1.28 | | | | | | | | 0.88 | | |
| PLP | β | 5.27 | 2.31 | 1.61 | | 1.28 | | | 2.05 | 5.36 | | 2.77 | 5.36 | | 2.05 | | 1.28 | | 0.88 |
| | α' | 4.30 | | | | | | | | | | 1.25 | | | | | 0.88 | | |
| G | α | 4.15 | | | | | | | | | | | | | | | | | |
| OOO | β | 5.27 | 2.31 | 1.61 | | 1.28 | | | 2.00 | | | 2.00 | | 1.28 | | | | | 0.88 |
| | α' | 4.30 | | | | | | | | 5.34 | | | | | | | | | |
| H | α | 4.15 | | | | | | | 2.04 | 5.34 | | 2.04 | | 1.27 | | | | | 0.88 |
| POO | β | 5.27 | 2.31 | 1.61 | | 1.28 | | | | | | | | | | | | | |
| | α' | 4.30 | | | | | | | | 1.27 | | | | | | | 0.88 | | |

A: trilineolein, B: 1-olein-2,3-dilinolein, C: 1-palmitin-2,3-dilinolein, D: 1,3-diolein-2-linolein, E: 1-palmitin-2-linolein-3-olein, F: 1,3-dipalmitin-2-linolein, G: triolein, H: 1-palmitin-2,3-diolein.

TABLE 10

¹³C-NMR spectral data of the compounds of Examples 2-9

| No. | Abb. | Gl-C | C-1 | C-2 | C-3 | C-4 | C-5 | C-6 | C-7 | C-8 | C-9 |
|---|---|---|---|---|---|---|---|---|---|---|---|
| A | α | 62.12 | 173.28 | 34.05 | 24.86 | | 29.05~29.62 | | | 27.21 | 130.01 |
| LLL | β | 68.91 | 172.87 | 34.21 | 24.90 | | | | | | 129.98 |
| B | α | 62.12 | 173.28 | 34.04 | 24.86 | | 29.07~29.79 | | | 27.22 | 130.03 |
| OLL | β | 68.89 | 172.87 | 34.21 | 24.90 | | | | | 27.19 | 130.00 |
| | α' | | 173.29 | | | | | | | | 129.73 |
| C | α | 62.12 | 173.30 | 34.04 | 24.89 | | 29.06~29.72 | | | 27.21 | 130.02 |
| PLL | β | 68.90 | 172.88 | 34.02 | 24.85 | | | | | | 129.99 |
| | α' | | 173.34 | 34.07 | 24.88 | | | | | | 29.06~29.71 |
| D | α | 62.12 | 173.29 | 34.05 | 24.86 | | 29.07~29.79 | | | 27.20 | 129.73 |
| OLO | β | 68.89 | 172.87 | 34.21 | 24.90 | | | | | 27.22 | 130.00 |
| E | α | 62.11 | 173.28 | 34.04 | 24.85 | | 29.06~29.78 | | | 27.18 | 129.71 |
| PLO | β | 68.91 | 172.86 | 34.20 | 24.87 | | | | | 27.21 | 129.98 |
| | α' | | 173.32 | 34.06 | 24.88 | | | | | | 29.06~29.78 |
| F | α | 62.09 | 173.32 | 34.05 | 24.86 | | 29.05~29.70 | | | | |
| PLP | β | 68.89 | 172.86 | 34.19 | 24.88 | | | | | 27.20 | 129.97 |
| G | α | 62.12 | 173.29 | 34.04 | 24.86 | | 29.07~9.78 | | | 27.19 | 129.72 |
| OOO | β | 68.90 | 172.87 | 34.21 | 24.90 | | | | | | 129.69 |
| H | α | 62.12 | 173.31 | 34.04 | 24.88 | | 29.06~29.78 | | | 27.19 | 129.72 |
| POO | β | 68.90 | 172.90 | 34.21 | 24.86 | | | | | | 129.69 |
| | α' | | 173.35 | 34.06 | 24.90 | | | | | | |

| No. | Abb. | C-10 | C-11 | C-12 | C-13 | C-14 | C-15 | C-16 | C-17 | C-18 |
|---|---|---|---|---|---|---|---|---|---|---|
| A | α | 128.08 | 25.64 | 127.91 | 130.22 | 27.21 | 29.05~29.62 | 31.53 | 22.58 | 14.07 |
| LLL | β | 128.09 | | 127.90 | | | | | | |
| B | α | 128.08 | 25.65 | 127.91 | 130.24 | 27.24 | 29.07~29.79 | 31.55 | 22.60 | 14.10 |
| OLL | β | 128.10 | | 127.90 | | | | | | |
| | α' | 130.03 | 27.22 | | | 29.07~29.79 | | 37.93 | 22.71 | 14.14 |
| C | α | 128.08 | 25.64 | 127.909 | 130.236 | | 29.06~29.72 | 31.54 | 22.59 | 14.09 |
| PLL | β | 128.09 | | | 130.236 | | | 31.55 | | |
| | α' | | | | | 31.95 | 22.71 | | | 14.14 |
| D | α | 130.03 | 27.24 | | | 29.07~29.79 | | 31.54 | 22.71 | 14.14 |
| OLO | β | 128.10 | 25.65 | 127.90 | 130.74 | 27.24 | 29.07~29.79 | 31.55 | 22.60 | 14.10 |
| E | α | 130.01 | 27.21 | | | 29.66~29.78 | | 31.92 | 22.69 | 14.12 |
| PLO | β | 128.09 | 25.64 | 127.903 | 30.22 | 27.23 | 29.06~29.78 | 31.53 | 22.58 | 14.07 |
| | α' | | | | | 31.94 | 22.71 | | | 14.12 |
| F | α | 29.05~29.70 | | | | 31.93 | 22.69 | | | 14.12 |
| PLP | β | 128.08 | 25.63 | 127.89 | 130.22 | 27.20 | 29.05~29.78 | 31.53 | 22.58 | 14.07 |
| G | α | 130.02 | 27.24 | | | 29.07~29.79 | | 31.92 | 22.70 | 14.12 |
| OOO | β | 130.03 | | | | | | | | |

TABLE 10-continued

¹³C-NMR spectral data of the compounds of Examples 2-9

| H | α | 130.02 | 27.24 | 29.06~29.78 | | 31.92 | | |
| POO | β | 130.03 | | | | | 22.70 | 14.12 |
| | α' | 29.06~29.78 | | | 31.94 | 22.70 | 14.12 | |

A: trilineolein, B: 1-olein-2,3-dilinolein, C: 1-palmitin-2,3-dilinolein, D: 1,3-diolein-2-linolein, E: 1-palmitin-2-linolein-3-olein, F: 1,3-dipalmitin-2-linolein, G: triolein, H: 1-palmitin-2,3-diolein.

Example 3 Preparation of 1-olein-2,3-dilinolein

Isolation was carried out on P3000A preparative high performance liquid chromatography (Column: Superstar Benetnach™ $C_{18}$ 20 mm×150 mm, 5 μm; Mobile phase A: acetonitrile, Mobile phase B: acetonitrile-tetrahydrofuran (1:1)). Coix seed oil solution was prepared with mobile phase B into 50 mg/mL, Injection volume of each separation was 1.5 mL. Gradient conditions: mobile phase B: 0-27 min: 50%-60%, 27-35 min: 90%, 35-45 min: 100%; Flow rate: 18 mL/min. UV detection wavelength: 208 nm. Peak fractions at retention time of 15.4-17.3 min were collected, and concentrated using a rotary evaporator in vacuum under nitrogen. Residues were transferred with chloroform to a 10 mL vial, and dried in a vacuum oven at 35° C. for 6 h. After filling with nitrogen, the dried samples were frozen in a refrigerator to give 1-olein-2,3-dilinolein.
HR-EI-MS: m/z=880.7518 (Calcd.=880.7520, $C_{55}H_{98}O_6$), Degree of unsaturation=7.
IR (KBr film): 1747, 1164, 1098; 2925, 2854, 723; 3008, 1655 cm¹ (weak).
¹H-NMR data are shown in Table 9.
¹³C-NMR data are shown in Table 10.

Example 4 Preparation of 1-palmitin-2,3-dilinolein

Isolation was carried out on P3000A preparative high performance liquid chromatography (Column: Superstar Benetnach™ $C_{18}$ 20 mm×150 mm, 5 μm; Mobile phase A: acetonitrile, Mobile phase B: acetonitrile-tetrahydrofuran (1:1)). Coix seed oil solution was prepared with mobile phase B into 50 mg/mL, Injection volume of each separation was 1.5 mL. Gradient conditions: mobile phase B: 0-27 min: 50%-60%, 27-35 min: 90%, 35-45 min: 100%; Flow rate: 18 mL/min. UV detection wavelength: 208 nm. Peak fractions at retention time of 17.4-18.1 min were collected, and concentrated using a rotary evaporator in vacuum under nitrogen to give a crude product.
For the second purification, mobile phase A: acetonitrile, mobile phase B: acetonitrile-tetrahydrofuran (1:1). Solution of the above crude product was prepared with mobile phase B into 20 mg/mL. Injection volume of each separation was 1.5 mL. Column: Superstar Benetnach™ $C_{18}$ (10 mm×250 mm, 5 μm); Gradient conditions: mobile phase B: 0-23 min: 50%-60%, 32-43 min: 60%-90%. 43-60 min: 100%; Flow rate: 3 mL/min; UV detection wavelength: 208 nm. Peak fractions at retention time of 31.2-34.7 min were collected, and concentrated using a rotary evaporator in vacuum under nitrogen. Residues were transferred with chloroform to a 10 mL vial, and dried in a vacuum oven at 35° C. for 6 h. After filling with nitrogen, the dried samples were frozen in a refrigerator to give the 1-palmitin-2,3-dilinolein.
HR-EI-MS: m/z=854.7370 (Calcd.=854.7363, $C_{55}H_{98}O_6$), Degree of unsaturation=7.
IR (KBr Film): 1746, 1165, 1095; 2926, 2854, 722; 3009, 1648 cm⁻¹ (weak).
¹H-NMR data are shown in Table 9.
¹³C-NMR data are shown in Table 10.

Example 5 Preparation of 1,3-diolein-2-linolein

Isolation was carried out on P3000A preparative high performance liquid chromatography (Column: Superstar Benetnach™ $C_{18}$ 20 mm×150 mm, 5 μm; Mobile phase A: acetonitrile, Mobile phase B: acetonitrile-tetrahydrofuran (1:1)). Coix seed oil solution was prepared with mobile phase B into 50 mg/mL. Injection volume of each separation was 1.5 mL. Gradient conditions: mobile phase B: 0-27 min: 50%-60%, 27-35 min: 90%, 35-45 min: 100%; Flow rate: 18 mL/min. UV detection wavelength: 208 nm. Peak fractions at retention time of 18.4-20.2 min were collected, and concentrated using a rotary evaporator in vacuum under nitrogen. Residues were transferred with chloroform to a 10 mL vial, and dried in a vacuum oven at 35° C. for 6 h. After filling with nitrogen, the dried samples were frozen in a refrigerator to give 1,3-diolein-2-linolein.
HR-EI-MS: m/z=882.7678 (Calcd.=882.7672, $C_{57}H_{102}O_6$), Degree of unsaturation=7.
IR (KBr film): 1747, 1163, 1097; 2925, 2855, 723; 3007, 1655 cm⁻¹ (weak).
¹H-NMR data are shown in Table 9.
¹³C-NMR data are shown in Table 10.

Example 6 Preparation of 1-palmitin-2-linolein-3-olein

Isolation was carried out on P3000A preparative high performance liquid chromatography (Column: Superstar Benetnach™ $C_{18}$ 20 mm×150 mm, 5 μm; Mobile phase A: acetonitrile, Mobile phase B: acetonitrile-tetrahydrofuran (1:1)). Coix seed oil solution was prepared with mobile phase B into 50 mg/mL. Injection volume of each separation was 1.5 mL. Gradient conditions: mobile phase B: 0-27 min: 50%-60%, 27-35 min: 90%, 35-45 min: 100%; Flow rate: 18 mL/min; UV detection wavelength: 208 nm. Peak fractions at retention time of 20.3-21.4 min were collected, and concentrated using a rotary evaporator in vacuum under nitrogen. Residues were transferred with chloroform to a 10 mL vial, and dried in a vacuum oven at 35° C. for 6 h. After filling with nitrogen, the dried samples were frozen in a refrigerator to give 1-palmitin-2-linolein-3-olein.
HR-EI-MS: m/z=856.7519 (Calcd.=856.7513, $C_{55}H_{100}O_6$), Degree of unsaturation=6.
IR (KBr film): 1747, 1164, 1098; 2925, 2854, 723; 3008, 1655 cm⁻¹ (weak).
¹H-NMR data are shown in Table 9.
¹³C-NMR data are shown in Table 10.

Example 7 Preparation of 1,3-dipalmitin-2-linolein

Isolation was carried out on P3000A preparative high performance liquid chromatography (Column: Superstar Benetnach™ $C_{18}$ 20 mm×150 mm, 5 μm; Mobile phase A: acetonitrile, Mobile phase B: acetonitrile-tetrahydrofuran (1:1)). Coix seed oil solution was prepared with mobile phase B into 50 mg/mL. Injection volume of each separation was 1.5 mL. Gradient conditions: mobile phase B: 0-27 min: 50%-60%, 27-35 min: 90%, 35-45 min: 100%; Flow rate: 18 mL/min. UV detection wavelength: 208 nm. Peak fractions at retention time of 25.7-26.2 min were collected, and concentrated using a rotary evaporator in vacuum under nitrogen. Residues were transferred with chloroform to a 10 mL vial, and dried in a vacuum oven at 35° C. for 6 h. After filling with nitrogen, the dried samples were frozen in a refrigerator to give 1,3-dipalmitin-2-linolein.

HR-EI-MS: m/z=830.7371 (Calcd=830.7363, $C_{53}H_{98}O_6$), Degree of unsaturation=5.

IR (KBr film): 1747, 1164, 1098; 2925, 2854, 723; 3008, 1655 cm$^{-1}$ (weak).

$^1$H-NMR data are shown in Table 9.
$^{13}$C-NMR data are shown in Table 10.

Example 8 Preparation of Triolein

Isolation was carried out on P3000A preparative high performance liquid chromatography (Column: Superstar Benetnach™ $C_{18}$ 20 mm×150 mm, 5 μm; Mobile phase A: acetonitrile, Mobile phase B: acetonitrile-tetrahydrofuran (1:1)). *Coix* seed oil solution was prepared with mobile phase B into 50 mg/mL. Injection volume of each separation was 1.5 mL. Gradient conditions: mobile phase B: 0-27 min: 50%-60%, 27-35 min: 90%, 35-45 min: 100%; Flow rate: 18 mL/min. UV detection wavelength: 208 nm. Peak fractions at retention time of 26.6-27.7 min were collected, and concentrated using a rotary evaporator in vacuum under nitrogen. Residues were transferred with chloroform to a 10 mL vial, and dried in a vacuum oven at 35° C. for 6 h. After filling with nitrogen, the dried samples were frozen in a refrigerator to give triolein.

HR-EI-MS: m/z=884.7851 (Calcd.=884.7833, $C_{57}H_{104}O_6$), Degree of unsaturation=6.

IR (KBr film): 1749, 1165, 1095; 2925, 2854, 723; 3004, 1654 cm$^{-1}$ (weak).

$^1$H-NMR data are shown in Table 9.
$^{13}$C-NMR data are shown in Table 10.

Example 9 Preparation of 1-palmitin-2,3-diolein

Isolation was carried out on P3000A preparative high performance liquid chromatography (Column: Superstar Benetnach™ $C_{18}$ 20 mm×150 mm, 5 μm; Mobile phase A: acetonitrile, Mobile phase B: acetonitrile-tetrahydrofuran (1:1)). *Coix* seed oil solution was prepared with mobile phase B into 50 mg/mL. Injection volume of each separation was 1.5 mL. Gradient conditions: mobile phase B: 0-27 min: 50%-60%, 27-35 min: 90%, 35-45 min: 100%; Flow rate: 18 mL/min. UV detection wavelength: 208 nm. Peak fractions at retention time of 28.2-29.3 min were collected, and concentrated using a rotary evaporator in vacuum under nitrogen to give crude product.

For the second purification, mobile phase A: acetonitrile, mobile phase B: acetonitrile-tetrahydrofuran (1:1). Solution of the above crude product was prepared with mobile phase B into 20 mg/mL. Injection volume of each separation was 1.5 mL. Column: Superstar Benetnach™ $C_{18}$ (10 mm×250 mm, 5 μm); Gradient conditions: mobile phase B: 0-23 min: 50%-60%, 32-43 min: 60%-90%, 43-60 min: 100%; Flow rate: 3 mL/min; UV detection wavelength: 208 nm. Peak fractions at retention time of 32.9-35.1 min were collected, and concentrated using a rotary evaporator in vacuum under nitrogen. Residues were transferred with chloroform to a 10 mL vial, and dried in a vacuum oven at 35° C. for 6 h. After filling with nitrogen, the dried samples were frozen in a refrigerator to give 1-palmitin-2,3-diolein.

HR-EI-MS: m/z=858.7672 (Calcd.=858.7676, $C_{55}H_{102}O_6$), Degree of unsaturation=5.

IR (KBr film): 1747, 1166, 1095; 2926, 2854, 722; 3003, 1654 cm$^{-1}$ (weak).

$^1$H-NMR data are shown in Table 9.
$^{13}$C-NMR data are shown in Table 10.

Example 10 Preparation of the Injection of the Pharmaceutical Composition

The composition contains following ingredients (in the mass percentage):

| | |
|---|---|
| trilinolein | 2.6 |
| 1-olein-2,3-dilinolein | 30.3 |
| 1-palmitin-2,3-dilinolein | 4.3 |
| 1,3-diolein-2-linolein | 27.9 |
| 1-palmitin-2-linolein-3-olein | 12.9 |
| 1,3-dipalmitin-2-linolein | 0.5 |
| triolein | 16 |
| 1-palmitin-2,3-diolein | 5.5 |

Formulation:

| | |
|---|---|
| The above composition | 100 g |
| Soybean lecithin for injection | 10 g |
| Glycerin for injection | 15 g |
| Water for injection adds to | 1000 mL |

Process:

To A formulated amount of soybean lecithin for injection was added an appropriate amount of water for injection. The mixture was dispersed with a high shear dispersing emulsifier into a dispersion without bulks or granules. Formulated amount of glycerin for injection was added. Then water for injection was added to a specified amount, and the mixture was stirred to give a water phase.

A formulated amount of the above composition was weighed. The weighed oil and the water phase prepared above were heated separately to 60° C., then mixed and emulsified in a high pressure homogenizer, in which the low pressure was 5 MPa and the high pressure was 25 MPa. The homogenization was repeated for 6 times until the amount of particles below 2 μm was no less than 95% and particles above 5 μm were undetectable. If necessary, NaOH or HCl was used to adjust the pH to 8.5.

The resulting homogeneous emulsion was filtered by nitrogen pressure through a microporous filter of 3 μm or less, then filled under nitrogen, and finally sterilized and cooled to afford the injection.

Example 11 Preparation of the Injection of the Pharmaceutical Composition

The composition contains following ingredients (in the mass percentage):

| | |
|---|---|
| trilinolein | 2.08 |
| 1-olein-2,3-dilinolein | 28.87 |
| 1-palmitin-2,3-dilinolein | 3.44 |
| 1,3-diolein-2-linolein | 32.09 |
| 1-palmitin-2-linolein-3-olein | 10.32 |
| 1,3-dipalmitin-2-linolein | 0.40 |
| triolein | 18.40 |
| 1-palmitin-2,3-diolein | 4.40 |

Formulation:

| | |
|---|---|
| The above composition | 300 g |
| Soybean lecithin acceptable for injection | 40 g |
| Glycerin acceptable for injection | 50 g |
| Water for injection adds to | 1000 mL |

Process:

To A formulated amount of soybean lecithin for injection was added an appropriate amount of water for injection. The mixture was dispersed with a high shear dispersing emulsifier into a dispersion without bulks or granules. Formulated amount of glycerin for injection was added. Then water for injection was added to a specified amount, and the mixture was stirred to give a water phase.

A formulated amount of the above composition was weighed. The weighed oil and the water phase prepared above were heated separately to 70° C., then mixed and emulsified in a high pressure homogenizer, in which the low pressure was 10 MPa and the high pressure was 50 MPa. The homogenization was repeated for 3 times until the amount of particles below 2 μm was no less than 95% and particles above 5 μm were undetectable. If necessary, NaOH or HCl was used to adjust the pH to 7.1.

The resulting homogeneous emulsion was filtered by nitrogen pressure through a microporous filter of 3 μm or less, then filled under nitrogen, and finally sterilized and cooled to afford the injection.

Example 12 Preparation of the Injection of the Pharmaceutical Composition

The composition contains following ingredients (in the mass percentage):

| | |
|---|---|
| trilinolein | 2.34 |
| 1-olein-2,3-dilinolein | 33.33 |
| 1-palmitin-2,3-dilinolein | 3.87 |
| 1,3-diolein-2-linolein | 29.05 |
| 1-palmitin-2-linolein-3-olein | 11.61 |
| 1,3-dipalmitin-2-linolein | 0.45 |
| triolein | 14.40 |
| 1-palmitin-2,3-diolein | 4.95 |

Formulation:

| | |
|---|---|
| The above composition | 200 g |
| Soybean lecithin for injection | 25 g |
| Glycerin acceptable for injection | 30 g |
| Water for injection adds to | 1000 mL |

Process:

To A formulated amount of soybean lecithin for injection was added an appropriate amount of water for injection. The mixture was dispersed with a high shear dispersing emulsifier into a dispersion without bulks or granules. Formulated amount of glycerin for injection was added. Then water for injection was added to a specified amount, and the mixture was stirred to give a water phase.

A formulated amount of the above composition was weighed. The weighed oil and the water phase prepared above were heated separately to 65° C., then mixed and emulsified in a high pressure homogenizer, in which the low pressure was 9 MPa and the high pressure was 35 MPa. The homogenization was repeated for 4 times until the amount of particles below 2 μm was no less than 95% and particles above 5 μm were undetectable. If necessary, NaOH or HCl was used to adjust the pH to 4.8.

The resulting homogeneous emulsion was filtered by nitrogen pressure through a microporous filter of 3 μm or less, then filled under nitrogen, and finally sterilized and cooled to afford the injection.

Example 13 Preparation of the Injection of the Pharmaceutical Composition

The composition contains following ingredients (in the mass percentage):

| | |
|---|---|
| trilinolein | 2.55 |
| 1-olein-2,3-dilinolein | 29.69 |
| 1-palmitin-2,3-dilinolein | 4.21 |
| 1,3-diolein-2-linolein | 29.34 |
| 1-palmitin-2-linolein-3-olein | 12.64 |
| 1,3-dipalmitin-2-linolein | 0.49 |
| triolein | 15.68 |
| 1-palmitin-2,3-diolein | 5.39 |

Formulation:

| | |
|---|---|
| The above composition | 150 g |
| Soybean lecithin acceptable for injection | 35 g |
| Glycerin for injection | 30 g |
| Water for injection adds to | 1000 mL |

Process:

To A formulated amount of soybean lecithin for injection was added an appropriate amount of water for injection. The mixture was dispersed with a high shear dispersing emulsifier into a dispersion without bulks or granules. Formulated amount of glycerin for injection was added. Then water for injection was added to a specified amount, and the mixture was stirred to give a water phase.

A formulated amount of the above composition was weighed. The weighed oil and the water phase prepared above were heated separately to 68° C., then mixed and emulsified in a high pressure homogenizer, in which the low pressure was 8 MPa and the high pressure was 40 MPa. The homogenization was repeated for 5 times until the amount of particles below 2 μm was no less than 95% and particles above 5 μm were undetectable. If necessary, NaOH or HCl was used to adjust the pH to 6.8.

The resulting homogeneous emulsion was filtered by nitrogen pressure through a microporous filter of 3 μm or less, then filled under nitrogen, and finally sterilized and cooled to afford the injection.

Example 14 Preparation of the Capsule of the Pharmaceutical Composition

The composition contains following ingredients (in the mass percentage):

| | |
|---|---|
| trilinolein | 2.65 |
| 1-olein-2,3-dilinolein | 29.91 |
| 1-palmitin-2,3-dilinolein | 4.39 |
| 1,3-diolein-2-linolein | 28.46 |
| 1-palmitin-2-linolein-3-olein | 13.16 |
| 1,3-dipalmitin-2-linolein | 0.51 |
| triolein | 15.32 |
| 1-palmitin-2,3-diolein | 5.61 |

Formulation:

| | |
|---|---|
| The above composition | 200 g |
| Vitamine E | 0.20 g |
| to give | 1000 capsules |

Process:

Glue formulation: Gelatin, purified water, glycerin and 10% ethylparaben solution were weighed at a weight ratio of 1:1.2:0.8:0.01. Glycerin, purified water and 10% ethylparaben solution were sequentially added into a glue melting tank and heated to 70° C. Then gelatin was added and constantly stirred under vacuum until the gelatin was completely dissolved. The glue was filtered and stored at 58° C. for use.

Drug liquid formulation: Formulated amount of the above composition and vitamin E were added into an ingredient tank and stirred constantly until thoroughly mixed.

Capsule pressing: Proper pellet dies were chosen according to the capsule size. Capsules were pressed under a temperature of 25° C. and a relative humidity of less than 35%, then shaped and dried. After excluding capsules of abnormal size, normal capsules were washed with 95% medicinal ethanol and dried continuously till the moisture content was less than 12%. Unqualified capsules were removed by visual inspection, and the final products were printed and packaged.

Example 15 Preparation of the Capsule of the Pharmaceutical Composition

The composition contains following ingredients (in the mass percentage):

| | |
|---|---|
| trilinolein | 2.86 |
| 1-olein-2,3-dilinolein | 27.27 |
| 1-palmitin-2,3-dilinolein | 4.37 |
| 1,3-diolein-2-linolein | 27.11 |
| 1-palmitin-2-linolein-3-olein | 14.19 |
| 1,3-dipalmitin-2-linolein | 0.55 |
| triolein | 17.60 |
| 1-palmitin-2,3-diolein | 6.05 |

Formulation:

| | | |
|---|---|---|
| The above composition | 800 | g |
| Tween 80 | 0.60 | g |
| to give | 1000 | capsules |

Process:

Glue formulation: Gelatin, purified water, glycerin and benzoic acid were weighed at a weight ratio of 1:1.2:0.8:0.01. Glycerin, purified water and benzoic acid were sequentially added into a glue melting tank and heated to 90° C. Then gelatin was added and constantly stirred under vacuum until the gelatin was completely dissolved. The glue was filtered and stored at 56° C. for use.

Drug liquid formulation: Formulated amount of the above composition and Tween 80 were added into an ingredient tank and stirred constantly until thoroughly mixed.

Capsule pressing: Proper pellet dies were chosen according to the capsule size. Capsules were pressed under a temperature of 20° C. and a relative humidity of less than 35%, then shaped and dried. After excluding capsules of abnormal size, normal capsules were washed with 95% medicinal ethanol and dried continuously till the moisture content was less than 12%. Unqualified capsules were removed by visual inspection, and the final products were printed and packaged.

Example 16 Preparation of the Capsule of the Pharmaceutical Composition

The composition contains following ingredients (in the mass percentage):

| | |
|---|---|
| trilinolein | 2.99 |
| 1-olein-2,3-dilinolein | 34.85 |
| 1-palmitin-2,3-dilinolein | 4.95 |
| 1,3-diolein-2-linolein | 22.32 |
| 1-palmitin-2-linolein-3-olein | 14.84 |
| 1,3-dipalmitin-2-linolein | 0.58 |
| triolein | 13.16 |
| 1-palmitin-2,3-diolein | 6.33 |

Formulation:

| | | |
|---|---|---|
| The above composition | 500 | g |
| Vitamine E | 0.40 | g |
| to give | 1000 | capsules |

Process:

Glue formulation: Gelatin, purified water, glycerin and potassium sorbate were weighed at a weight ratio of 1:0.9:0.6:0.005. Glycerin, purified water and potassium sorbate were sequentially added into a glue melting tank and heated to 80° C. Then gelatin was added and constantly stirred under vacuum until the gelatin was completely dissolved. The glue was filtered and stored at 62° C. for use.

Drug liquid formulation: Formulated amount of the above composition and Vitamine E were added into an ingredient tank and stirred constantly until thoroughly mixed.

Capsule pressing: Proper pellet dies were chosen according to the capsule size. Capsules were pressed under a temperature of 30° C. and a relative humidity of less than 35%, then shaped and dried. After excluding capsules of abnormal size, normal capsules were washed with 95% medicinal ethanol and dried continuously till the moisture content was less than 12%. Unqualified capsules were removed by visual inspection, and the final products were printed and packaged.

Example 17 Preparation of the Capsule of the Pharmaceutical Composition

The composition contains following ingredients (in the mass percentage):

| | |
|---|---|
| trilinolein | 2.73 |
| 1-olein-2,3-dilinolein | 30.35 |
| 1-palmitin-2,3-dilinolein | 4.31 |
| 1,3-diolein-2-linolein | 28.08 |
| 1-palmitin-2-linolein-3-olein | 12.65 |
| 1,3-dipalmitin-2-linolein | 0.49 |
| triolein | 15.98 |
| 1-palmitin-2,3-diolein | 5.41 |

Formulation:

| | | |
|---|---|---|
| The above composition | 600 | g |
| Tween 80 | 0.3 | g |
| to give | 1000 | capsules |

Process:

Glue formulation: Gelatin, purified water, glycerin and chlorhexidine acetate were weighed at a weight ratio of 1:1.0:0.5:0.008. Glycerin, purified water and chlorhexidine acetate were sequentially added into a glue melting tank and heated to 85° C. Then gelatin was added and constantly stirred under vacuum until the gelatin was completely dissolved. The glue was filtered and stored at 56° C. for use.

Drug liquid formulation: Formulated amount of the above composition and Tween 80 were added into an ingredient tank and stirred constantly until thoroughly mixed.

Capsule pressing: Proper pellet dies were chosen according to the capsule size. Capsules were pressed under a temperature of 18° C. and a relative humidity of less than 35%, then shaped and dried. After excluding capsules of abnormal size, normal capsules were washed with 95% medicinal ethanol and dried continuously till the moisture content was less than 12%. Unqualified capsules were removed by visual inspection, and the final products were printed and packaged.

Example 18 Preparation of the Injection of the Pharmaceutical Composition

The composition contains following ingredients (in the mass percentage):

| | |
|---|---|
| trilinolein | 2.18 |
| 1-olein-2,3-dilinolein | 30.09 |
| 1-palmitin-2,3-dilinolein | 3.65 |
| 1,3-diolein-2-linolein | 30.63 |
| 1-palmitin-2-linolein-3-olein | 10.87 |
| 1,3-dipalmitin-2-linolein | 0.42 |
| triolein | 17.76 |
| 1-palmitin-2,3-diolein | 4.40 |

Formulation:

| | |
|---|---|
| The above composition | 100 g |
| Soybean lecithin for injection | 10 g |
| Glycerin for injection | 15 g |
| Water for injection adds to | 1000 mL |

Process:

To A formulated amount of soybean lecithin for injection was added an appropriate amount of water for injection. The mixture was dispersed with a high shear dispersing emulsifier into a dispersion without bulks or granules. Formulated amount of glycerin for injection was added. Then water for injection was added to a specified amount, and the mixture was stirred to give a water phase.

A formulated amount of the above composition was weighed. The weighed oil and the water phase prepared above were heated separately to 60° C., then mixed and emulsified in a high pressure homogenizer, in which the low pressure was 6 MPa and the high pressure was 28 MPa. The homogenization was repeated for 4 times until the amount of particles below 2 μm was no less than 95% and particles above 5 μm were undetectable. If necessary, NaOH or HCl was used to adjust the pH to 6.8.

The resulting homogeneous emulsion was filtered by nitrogen pressure through a microporous filter of 3 μm or less, then filled under nitrogen, and finally sterilized and cooled to afford the injection.

Example 19 Preparation of the Injection of the Pharmaceutical Composition

The composition contains following ingredients (in the mass percentage):

| | |
|---|---|
| trilinolein | 2.46 |
| 1-olein-2,3-dilinolein | 31.77 |
| 1-palmitin-2,3-dilinolein | 4.09 |
| 1,3-diolein-2-linolein | 29.35 |
| 1-palmitin-2-linolein-3-olein | 12.01 |
| 1,3-dipalmitin-2-linolein | 0.48 |
| triolein | 14.82 |
| 1-palmitin-2,3-diolein | 5.02 |

Formulation:

| | |
|---|---|
| The above composition | 300 g |
| Soybean lecithin acceptable for injection | 40 g |
| Glycerin acceptable for injection | 50 g |
| Water for injection adds to | 1000 mL |

Process:

To A formulated amount of soybean lecithin acceptable for injection was added an appropriate amount of water for injection. The mixture was dispersed with a high shear dispersing emulsifier into a dispersion without bulks or granules. Formulated amount of glycerin acceptable for injection was added. Then water for injection was added to a specified amount, and the mixture was stirred to give a water phase.

A formulated amount of the above composition was weighed. The weighed oil and the water phase prepared above were heated separately to 70° C., then mixed and emulsified in a high pressure homogenizer, in which the low pressure was 11 MPa and the high pressure was 46 MPa. The homogenization was repeated for 5-6 times until the amount of particles below 2 μm was no less than 95% and particles above 5 μm were undetectable. If necessary, NaOH or HCl was used to adjust the pH to 7.5.

The resulting homogeneous emulsion was filtered by nitrogen pressure through a microporous filter of 3 μm or less, then filled under nitrogen, and finally sterilized and cooled to afford the injection.

Example 20 Preparation of the Injection of the Pharmaceutical Composition

The composition contains following ingredients (in the mass percentage):

| | |
|---|---|
| trilinolein | 2.60 |
| 1-olein-2,3-dilinolein | 29.84 |
| 1-palmitin-2,3-dilinolein | 4.30 |
| 1,3-diolein-2-linolein | 25.76 |
| 1-palmitin-2-linolein-3-olein | 13.90 |
| 1,3-dipalmitin-2-linolein | 0.50 |
| triolein | 17.23 |
| 1-palmitin-2,3-diolein | 5.87 |

Formulation:

| | |
|---|---|
| The above composition | 200 g |
| Soybean lecithin for injection | 25 g |
| Glycerin acceptable for injection | 30 g |
| Water for injection adds to | 1000 mL |

Process:

To A formulated amount of soybean lecithin for injection was added an appropriate amount of water for injection. The mixture was dispersed with a high shear dispersing emulsifier into a dispersion without bulks or granules. Formulated amount of glycerin acceptable for injection was added. Then water for injection was added to a specified amount, and the mixture was stirred to give a water phase.

A formulated amount of the above composition was weighed. The weighed oil and the water phase prepared above were heated separately to 65° C., then mixed and emulsified in a high pressure homogenizer, in which the low pressure was 9 MPa and the high pressure was 36 MPa. The homogenization was repeated for 3 times until the amount of particles below 2 μm was no less than 95% and particles above 5 μm were undetectable. If necessary, NaOH or HCl was used to adjust the pH to 6.5.

The resulting homogeneous emulsion was filtered by nitrogen pressure through a microporous filter of 3 μm or less, then filled under nitrogen, and finally sterilized and cooled to afford the injection.

Example 21 Preparation of the Capsule of the Pharmaceutical Composition

The composition contains following ingredients (in the mass percentage):

| | |
|---|---|
| trilinolein | 2.71 |
| 1-olein-2,3-dilinolein | 31.22 |
| 1-palmitin-2,3-dilinolein | 1.51 |
| 1,3-diolein-2-linolein | 29.31 |
| 1-palmitin-2-linolein-3-olein | 13.87 |
| 1,3-dipalmitin-2-linolein | 0.53 |
| triolein | 14.95 |
| 1-palmitin-2,3-diolein | 5.90 |

Formulation:

| | |
|---|---|
| The above composition | 200 g |
| Vitamine E | 0.20 g |
| to give | 1000 capsules |

Process:

Glue formulation: Gelatin, purified water, glycerin and 10% ethylparaben solution were weighed at a weight ratio of 1:1.2:0.8:0.01. Glycerin, purified water and 10% ethylparaben solution were sequentially added into a glue melting tank and heated to 70° C. Then gelatin was added and constantly stirred under vacuum until the gelatin was completely dissolved. The glue was filtered and stored at 60° C. for use.

Drug liquid formulation: Formulated amount of the above composition and Vitamine E were added into an ingredient tank and stirred constantly until thoroughly mixed.

Capsule pressing: Proper pellet dies were chosen according to the capsule size. Capsules were pressed under a temperature of 28° C. and a relative humidity of less than 35%, then shaped and dried. After excluding capsules of abnormal size, normal capsules were washed with 95% medicinal ethanol and dried continuously till the moisture content was less than 12%. Unqualified capsules were removed by visual inspection, and the final products were printed and packaged.

Example 22 Preparation of the Capsule of the Pharmaceutical Composition

The composition contains following ingredients (in the mass percentage):

| | |
|---|---|
| trilinolein | 2.92 |
| 1-olein-2,3-dilinolein | 25.68 |
| 1-palmitin-2,3-dilinolein | 4.81 |
| 1,3-diolein-2-linolein | 29.16 |
| 1-palmitin-2-linolein-3-olein | 14.84 |
| 1,3-dipalmitin-2-linolein | 0.57 |
| triolein | 15.95 |
| 1-palmitin-2,3-diolein | 6.07 |

Formulation:

| | |
|---|---|
| The above composition | 800 g |
| Tween 80 | 0.60 g |
| to give | 1000 capsules |

Process:

Glue formulation: Gelatin, purified water, glycerin and benzoic acid were weighed at a weight ratio of 1:1.2:0.8:0.01. Glycerin, purified water and benzoic acid were sequentially added into a glue melting tank and heated to 90° C. Then gelatin was added and constantly stirred under vacuum until the gelatin was completely dissolved. The glue was filtered and stored at 56° C. for use.

Drug liquid formulation: Formulated amount of the above composition and Tween 80 were added into an ingredient tank and stirred constantly until thoroughly mixed.

Capsule pressing: Proper pellet dies were chosen according to the capsule size. Capsules were pressed under a temperature of 16° C. and a relative humidity of less than 35%, then shaped and dried. After excluding capsules of abnormal size, normal capsules were washed with 95% medicinal ethanol and dried continuously till the moisture content was less than 12%. Unqualified capsules were removed by visual inspection, and the final products were printed and packaged.

Example 23 Preparation of the Capsule of the Pharmaceutical Composition

The composition contains following ingredients (in the mass percentage):

| | |
|---|---|
| trilinolein | 2.99 |
| 1-olein-2,3-dilinolein | 24.39 |
| 1-palmitin-2,3-dilinolein | 4.95 |
| 1,3-diolein-2-linolein | 31.25 |
| 1-palmitin-2-linolein-3-olein | 14.70 |
| 1,3-dipalmitin-2-linolein | 0.58 |
| triolein | 14.98 |
| 1-palmitin-2,3-diolein | 6.17 |

Formulation:

| | |
|---|---|
| The above composition | 500 g |
| Vitamine E | 0.40 g |
| to give | 1000 capsules |

Process:

Glue formulation: Gelatin, purified water, glycerin and potassium sorbate were weighed at a weight ratio of 1:0.9:0.6:0.005. Glycerin, purified water and potassium sorbate were sequentially added into a glue melting tank and heated to 80° C. Then gelatin was added and constantly stirred under vacuum until the gelatin was completely dissolved. The glue was filtered and stored at 61° C. for use.

Drug liquid formulation: Formulated amount of the above composition and Vitamine E were added into an ingredient tank and stirred constantly until thoroughly mixed.

Capsule pressing: Proper pellet dies were chosen according to the capsule size. Capsules were pressed under a temperature of 22° C. and a relative humidity of less than 35%, then shaped and dried. After excluding capsules of abnormal size, normal capsules were washed with 95% medicinal ethanol and dried continuously till the moisture content was less than 12%. Unqualified capsules were removed by visual inspection, and the final products were printed and packaged.

What is claimed is:

1. A pharmaceutical composition, comprising 8 ingredients in the following mass percentages:

| | |
|---|---|
| trilinolein | 2.08-2.99 |
| 1-olein-2,3-dilinolein | 24.24-34.85 |
| 1-palmitin-2,3-dilinolein | 3.44-4.95 |
| 1,3-diolein-2-linolein | 22.32-32.09 |
| 1-palmitin-2-linolein-3-olein | 10.32-14.84 |
| 1,3-dipalmitin-2-linolein | 0.40-0.58 |
| triolein | 12.80-18.40 |
| 1-palmitin-2,3-diolein | 4.40-6.33 |

Wherein said 8 ingredients are obtained by alkali-refining from a crude *coix* seed oil which is extracted from *coix* seed powder by supercritical $CO_2$ extraction.

2. The pharmaceutical composition of claim 1, wherein said ingredients are in the following mass percentages:

| | |
|---|---|
| trilinolein | 2.34-2.86 |
| 1-olein-2,3-dilinolein | 27.27-33.33 |
| 1-palmitin-2,3-dilinolein | 3.87-4.73 |
| 1,3-diolein-2-linolein | 25.11-30.69 |
| 1-palmitin-2-linolein-3-olein | 11.61-14.19 |
| 1,3-dipalmitin-2-linolein | 0.45-0.55 |
| triolein | 14.40-18.40 |
| 1-palmitin-2,3-diolein | 4.95-6.05. |

3. The pharmaceutical composition of claim 1, wherein said ingredients are in the following mass percentages:

| | |
|---|---|
| trilinolein | 2.55-2.65 |
| 1-olein-2,3-dilinolein | 29.69-30.91 |
| 1-palmitin-2,3-dilinolein | 4.21-4.39 |
| 1,3-diolein-2-linolein | 27.34-28.46 |
| 1-palmitin-2-linolein-3-olein | 12.64-13.16 |
| 1,3-dipalmitin-2-linolein | 0.49-0.51 |
| triolein | 15.68-16.32 |
| 1-palmitin-2,3-diolein | 5.39-5.61. |

4. A pharmaceutical preparation, comprising a therapeutically effective amount of the pharmaceutical composition of claim 1 and one or more pharmaceutically acceptable carriers, wherein said pharmaceutically acceptable carriers are selected from pharmaceutical dilutions, excipients, fillers, emulsifiers, binders, absorption accelerators, surfactants, disintegrants, lubricants and antioxidants, flavoring agents, sweeteners, preservatives and/or coloring agents.

5. The pharmaceutical preparation of claim 4, wherein the pharmaceutically acceptable carriers are selected from one or more in the group consisting of: mannitol, sorbitol, sodium metabisulfite, sodium bisulfite, sodium thiosulfate, cysteine hydrochloride, thioglycolic acid, methionine, soybean lecithin, vitamin C, vitamin E, EDTA disodium, EDTA calcium sodium, a monovalent alkali metal carbonate, acetate, phosphate or its aqueous solution, hydrochloric acid, acetic acid, sulfuric acid, phosphoric acid, amino acids, sodium chloride, potassium chloride, sodium lactate, ethylparaben solution, benzoic acid, potassium sorbate, chlorhexidine acetate, xylitol, maltose, glucose, fructose, dextran, glycine, starch, sucrose, lactose, mannitol, silicic derivatives, cellulose and its derivatives, alginates, gelatin, polyvinyl pyrrolidone, glycerin, Tween 80, agar-agar, calcium carbonate, calcium bicarbonate, surfactant, polyethylene glycol, cyclodextrin, β-cyclodextrin, phospholipid material, kaolin, talc, and calcium stearate or magnesium stearate.

6. The pharmaceutical preparation of claim 4, wherein said pharmaceutical preparation is an oral solid preparation, an oral liquid preparation, or an injection.

7. The pharmaceutical preparation of claim 6, wherein:

said oral solid preparation is selected from any one of capsules, tablets, dripping pills, granules, and concentrated pills;

said oral liquid preparation is selected from any one of aqueous or oily suspensions, solutions, emulsions, syrups or elixirs, and a dry product that can be reconstructed by water or other suitable carrier before use; and said injection is selected from any one of nano suspensions, liposomes, emulsions, lyophilized powder for injection and aqueous injection.

8. The pharmaceutical preparation of claim 6, wherein said injection comprises the following components:

| | |
|---|---|
| Composition of the invention | 50-350 g |
| Soybean lecithin for Injection or soybean lecithin acceptable for injection | 10-40 g |
| Glycerin for Injection or glycerin acceptable for injection | 15-50 g |
| Water for injection adds to | 1000 mL. |

9. The pharmaceutical preparation of claim 8, which is prepared by a method comprising steps of:

adding appropriate amount of water for injection to soybean lecithin for injection or soybean lecithin acceptable for injection; dispersing the mixture with a high shear dispersing emulsifier to give a dispersion without bulks or granules; adding glycerin for injection or glycerin acceptable for injection; then adding water for injection to a specified amount, and stirring the mixture to give a water phase;

weighing the pharmaceutical composition of the invention; heating the weighed oil and the water phase separately to 60-70▨,, then mixing them and emulsifying the mixture in a high pressure homogenizer, in which the low pressure is 5-12 MPa and the high pressure is 25-50 MPa; repeating the cycle of homogenization for 3-6 times until the amount of particles below 2 μm is no less than 95% and particles above 5 μm are undetectable; using NaOH or HCl to adjust the pH to 4.8 to 8.5; and filtering the resulting homogeneous emulsion by nitrogen pressure through a microporous filter of 3 μm or less; filling the emulsion with nitrogen, sterilizing and cooling to afford the injection.

10. The pharmaceutical preparation of claim 6, wherein said oral solid preparation comprises the following components:

| Composition of the invention | 200-800 g |
| Antioxidant(s) and/or emulsifier(s) | 0.20-0.60 g |
| to give | 1000 capsules. |

11. The pharmaceutical preparation of claim 10, which is prepared by a method comprising steps of:
preparing glue solution: weighing gelatin, purified water, glycerin and a preservative at a weight ratio of 1:0.6-1.2:0.3-0.8:0.0001-0.01; adding glycerin, purified water and preservative sequentially into a glue melting tank; heating to 70▫, -90▫,; then adding gelatin and constantly stirring the mixture under vacuum until the gelatin is completely dissolved; filtering the glue solution and storing the filtered glue solution at 56-62° C. for use;
preparing drug liquid: adding the above composition, antioxidant(s) and/or emulsifier(s) into an dosing tank, and stirring the mixture constantly until being homogeneously mixed; and
pressing capsules: choosing proper pellet dies according to the capsule size; pressing capsules in a temperature of 15-30▫, and a relative humidity of less than 35%; drying the pressed and shaped capsules; after removing capsules of abnormal size, washing the normal capsules with 95% medicinal ethanol, and drying them continuously to a moisture content of less than 12%; visually inspecting and removing unqualified capsules; finally printing and packaging to afford the pharmaceutical preparation.

12. The pharmaceutical preparation of claim 11, wherein:
said preservative is selected from any one of 10% ethylparaben solution, benzoic acid, potassium sorbate and chlorhexidine acetate;
said antioxidant is vitamin E; and
said emulsifier is Tween 80.

13. A method of the treatment of a tumor or the enhancement of immunity in a mammal, comprising administering to a mammal in need a therapeutically effective amount of the pharmaceutical composition of claim 1.

14. The method of claim 13, wherein said pharmaceutical composition is administered in combination with LAK cells.

15. The method of claim 13, wherein said tumor is selected from a group consisting of lung cancer, liver cancer, pancreatic cancer, prostate cancer, ovarian cancer and breast cancer, in early, middle or late stage.

16. A method of the treatment of a tumor or the enhancement of immunity in a mammal, comprising administering to a mammal in need a therapeutically effective amount of the pharmaceutical preparation of claim 4.

17. The method of claim 13, wherein said pharmaceutical preparation is administered in combination with LAK cells.

18. The method of claim 16, wherein said tumor is selected from a group consisting of lung cancer, liver cancer, pancreatic cancer, prostate cancer, ovarian cancer and breast cancer, in early, middle or late stage.

* * * * *